United States Patent [19]
Schwab et al.

[11] Patent Number: 5,383,850
[45] Date of Patent: Jan. 24, 1995

[54] INHALER

[75] Inventors: Egon Schwab, Hochheim am Main; Hans-Joachim Loos, Ginsheim-Gustavsburg; Günter Ziegert, Frankfurt am Main, all of Germany

[73] Assignee: Hoechst Aktiengesellschaft, Frankfurt am Main, Germany

[21] Appl. No.: 72,326

[22] Filed: Jun. 3, 1993

[30] Foreign Application Priority Data

Jun. 5, 1992 [DE] Germany ............... 4218517

[51] Int. Cl.6 .............. A61M 13/00; A61M 15/00; A61M 16/00; B05D 7/14
[52] U.S. Cl. ................. 604/58; 128/203.15; 222/636
[58] Field of Search ......... 604/58; 128/200.17, 128/203.15; 222/370, 636, 637; 406/49

[56] References Cited

U.S. PATENT DOCUMENTS

| | | | |
|---|---|---|---|
| 2,590,832 | 3/1952 | Brown | 604/58 |
| 5,048,514 | 9/1991 | Ramella | 128/203.15 |
| 5,094,403 | 3/1992 | Tschumi | 222/370 |
| 5,201,308 | 4/1993 | Newhouse | 128/203.15 |
| 5,243,970 | 9/1993 | Ambrosio et al. | 128/203.15 |
| 5,301,666 | 4/1994 | Lerk et al. | 128/203.15 |

FOREIGN PATENT DOCUMENTS

| | | |
|---|---|---|
| 0451745 | 10/1992 | European Pat. Off. |
| WO90/07351 | 7/1990 | WIPO |
| WO91/06333 | 5/1991 | WIPO |
| 9204068 | 3/1992 | WIPO .............. 604/58 |
| 9204928 | 4/1992 | WIPO .............. 604/58 |

Primary Examiner—C. Fred Rosenbaum
Assistant Examiner—Frank Wilkens, III
Attorney, Agent, or Firm—Curtis, Morris & Safford

[57] ABSTRACT

In the inhaler for the repeated inhalation of powdered pharmaceuticals there is arranged, in a housing (13) which has a rotatable cap (4), a dosing wheel with dosing chambers (22) between the intermediate floor (21) and a frame (20), which is supported on the baseplate (14). The rotatable cap (4), which is supported on the lid (17) by means of a spring (12), has an axially arranged cylinder (7) which projects through the lid (17), the intermediate floor (21) and the frame (20) into the housing (13) and is the drive shaft for the dosing wheel (1). The housing (13) is provided with a supply chamber (2) whose bottom part (intermediate floor (21)) has an opening (23) whose cross-section corresponds to that of the dosing chambers (22). The baseplate (14) is provided with a mouthpiece (9) which is arranged in a radial direction and which has a blow-out channel (6) with valve (8), which channel opens out into a tubular piston (16) which is fixed to the baseplate (14) and which extends into the cylinder (7) and connects the blow-out channel (6) with the inner space of the cylinder (7) via an opening (24). The frame (20) has a shaft (5) which connects the dosing chambers (22) with the blow-out channel (6) via an opening (25) in the mouthpiece (9).

9 Claims, 1 Drawing Sheet

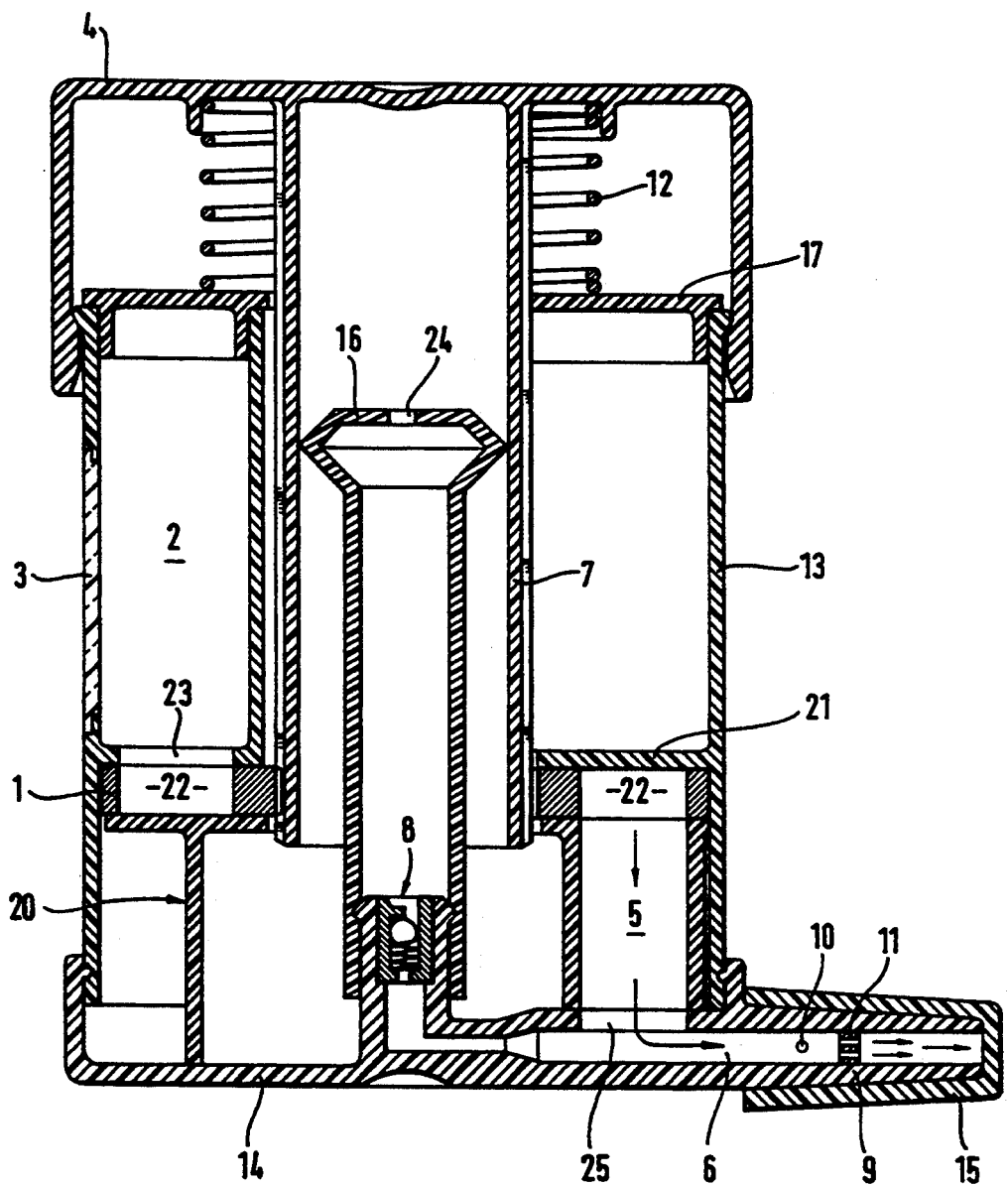

INHALER

BACKGROUND OF THE INVENTION

The invention relates to an inhaler for the repeated inhalation of pulverulent pharmaceuticals.

Inhalation appliances of the said type are known. Disadvantages of these appliances are their complicated mechanical construction and the tendency to form conglomerates, as a consequence of air humidity, which can penetrate into their channel system. The invention aims to provide a remedy for these problems.

SUMMARY OF THE INVENTION

The invention achieves the object by means of an inhaler having the features of the claim 1.

The whirling-up of the pharmaceuticals in the blow-out channel can be further improved by drilled holes extending radially in the mouthpiece and by a nebulizing device in the blow-out channel. The pharmaceutical supply can be checked through a viewing window in the supply chamber.

As well as practical handling, the inhaler permits optimal dosing accuracy. It can be adjusted to the dosing requirements by the simple exchange of the dosing wheel. It does not require maintenance and can be easily cleaned.

BRIEF DESCRIPTION OF THE INVENTION

The invention will best be understood from the following detailed description when studied with the accompanying FIGURE which shows a longitudinal sectional view of an inhaler of the invention.

DETAILED DESCRIPTION OF THE INVENTION

An embodiment example of the invention is portrayed in the FIGURE and is described in more detail below:

The housing (13) has an intermediate floor (21) and is closed with a lid (17) and a baseplate (14). A rotatable cap (4) is supported on the lid (17) via a spring (12), the edge of which cap encloses the upper edge of the housing wall. The rotatable cap (4) has an axially arranged cylinder (7) which projects through the lid (17), the intermediate floor (21) and a frame (20) into the housing (13). The cylinder (7) is, at the same time, the drive shaft for a dosing wheel (1) which has dosing chambers (22) and which is arranged in the housing (13) concentrically relative to the cylinder (7) and between intermediate floor (21) and frame (20). The housing (13) has a supply chamber (2) for the pharmaceutical which, for its part, can be contained in a cartridge. The supply chamber is provided with a viewing window (3) and has an opening (23) whose cross-section corresponds to that of the dosing chamber (22). The baseplate (14) is provided with a mouthpiece (9) which extends radially and contains a blow-out channel (6) with valve (8). The blow-out channel (6) can be closed at one end with a cap (15) and opens out by the other end into a tubular piston (16) which extends into the cylinder (7), starting from the baseplate (14). The blow-out channel (6) is connected for flow with the inner space of the cylinder (7) via an opening (24) and valve (8). The frame (20) has a shaft (5) which connects the dosing chambers (22) with the blow-out channel (6) via a corresponding opening (25) in the mouthpiece (9). The mouthpiece (9) can be provided with drilled holes (10) which run radially and which open out into the blow-out channel (6). The blow-out channel (6) can have a nebulizing device (sieve plate) (11). The pharmaceutical falls through opening (23) out of the supply chamber (2) into the dosing chamber (22) of the dosing wheel (1). By means of rotating the rotatable cap (4), the metered quantity of powder is transported to the discharge shaft (5), and falls through this via opening (25) into the blow-out channel (6). Administration takes place by pressing down the rotatable cap (4) to the limit stop, as a result of which the air present in the cylinder (7) is compressed up to a defined pressure. Once the pressure has been reached, valve (8) opens and releases the compressed air. The air is forced into the blow-out channel (6), in which the powder deposited therein is swirled up by the air stream and blown in the direction of the mouthpiece (9). In the mouthpiece (9) there are located lateral drilled holes (10) which, during inhalation by the patient, produce an injector effect in the blow-out channel. Powder conglomerates, such as occur in fine powders, are flung by the air stream, which can be amplified by the injector effect, against a nebulizing device (i.e. sieve plate) (11) where they are broken up and micronized. The baseplate (14) with mouthpiece (9) is detachable, so that the latter can be cleaned when necessary. In order to prevent the dose from being doubled, the inhaler is provided with a blocking device (e.g. a coupling which disengages on pressing down the rotatable cap—not shown), so that a new dosing can only take place once the blow-out process is complete. After the blow-out process, the rotatable cap (4) is returned again to the starting position by spring (12).

We claim:

1. An inhaler for the repeated inhalation of a pulverulent pharmaceutical, comprising
   a) a housing having a first end and a second end, and a means defining a hollow cylinder axially disposed within the housing, said hollow cylinder having a first end and a second end;
   b) an lid detachably attached to the first end of the housing;
   c) an intermediate floor disposed between the first and second end of the housing;
   d) means defining a housing chamber defined by the hollow cylinder, the housing, the lid and the intermediate floor for containing the pulverulent pharmaceutical;
   e) the hollow cylinder first end being attached to a rotatable cap which operationally engages the first end of the housing;
   f) a biasing means disposed between the lid and the rotatable cap;
   g) a baseplate, attached to the second end of the housing, having means defining a hollow mouthpiece which has a first end and a second end and means defining a blow-out channel defined by an interior surface of the hollow mouthpiece, the hollow mouthpiece first end, and the hollow mouthpiece second end;
   h) means defining a mouthpiece opening between the first and second mouthpiece end;
   i) the first mouthpiece end having a valving means;
   j) a piston means, attached to the first mouthpiece end, operationally and axially disposed within the hollow cylinder;
   k) a frame, attached to the baseplate, disposed within the housing;

l) an dosing wheel, having means defining at least one dosing chamber extending through the dosing wheel, disposed between the intermediate floor and the frame;

m) the hollow cylinder, projecting from the rotatable cap through the lid, the intermediate floor, and the frame, operationally engaging the dosing wheel for rotating the dosing wheel between a loading and an unloading position, n) the intermediate floor having means defining a loading hole for transferring the pulverulent pharmaceutical from the housing chamber to the dosing chamber while the dosing wheel is in the loading position; and o) the frame having a discharge shaft operationally engaging the mouthpiece at the mouthpiece opening thereby connecting the dosing chamber, while in an unloading position, to the blow-out channel.

2. The inhaler as claimed in claim 1, further comprising means defining a supply chamber between the housing, the hollow cylinder, the intermediate floor, and the lid, defined by two walls radially connecting the housing and the hollow cylinder.

3. The inhaler as claimed in claim 1, wherein the mouthpiece has a nebulizing device disposed within the mouthpiece between the opening and the mouthpiece second end.

4. The inhaler as claimed in claim 3, wherein the mouthpiece has means defining at least one hole disposed between the opening and the nebulizing device.

5. The inhaler as claimed in claim 1, wherein the housing further comprises a substantially transparent or translucent panel.

6. The inhaler as claimed in claim 1, wherein the lid is annular.

7. The inhaler as claimed in claim 1, wherein the intermediate floor is annular.

8. The inhaler as claimed in claim 1, wherein the biasing means is a spring.

9. The inhaler as claimed in claim 1, wherein the lid is annular and the intermediate floor is annular.

* * * * *